United States Patent [19]
Oroskar

[11] Patent Number: 5,856,606
[45] Date of Patent: Jan. 5, 1999

[54] TURBULENT BED SOLID CATALYST HYDROCARBON ALKYLATION PROCESS

[75] Inventor: Anil R. Oroskar, Downers Grove, Ill.

[73] Assignee: UOP LLC, Des Plaines, Ill.

[21] Appl. No.: 723,207

[22] Filed: Sep. 27, 1996

[51] Int. Cl.⁶ .............. C07C 2/64; C07C 2/56; C07C 2/58
[52] U.S. Cl. .............. 585/446; 585/447; 585/467; 585/450; 585/709; 585/719; 585/721
[58] Field of Search .............. 585/446, 447, 585/467, 450, 709, 719, 721

[56] References Cited

U.S. PATENT DOCUMENTS

| | | | |
|---|---|---|---|
| 3,655,813 | 4/1972 | Kirsch et al. | 260/683.43 |
| 3,726,941 | 4/1973 | Randall et al. | 585/707 |
| 4,134,734 | 1/1979 | Winter, III | 585/447 |
| 4,139,573 | 2/1979 | Carson | 260/683.49 |
| 4,827,069 | 5/1989 | Kushnerick et al. | 585/415 |
| 4,849,569 | 7/1989 | Smith, Jr. | 585/446 |
| 4,950,834 | 8/1990 | Arganbright et al. | 585/446 |
| 5,019,669 | 5/1991 | Adams et al. | 585/450 |
| 5,086,193 | 2/1992 | Sy | 585/446 |
| 5,087,784 | 2/1992 | Primack et al. | 585/446 |
| 5,133,942 | 7/1992 | Jones | 422/142 |
| 5,157,158 | 10/1992 | Terna Tejero et al. | 585/467 |
| 5,252,613 | 10/1993 | Chang et al. | 518/700 |
| 5,310,713 | 5/1994 | Kojima et al. | 585/721 |
| 5,489,732 | 2/1996 | Zhang et al. | 585/467 |
| 5,523,503 | 6/1996 | Funk et al. | 585/446 |
| 5,672,798 | 9/1997 | Zhang et al. | 585/467 |

*Primary Examiner*—Mark L. Bell
*Assistant Examiner*—Patricia L. Hailey
*Attorney, Agent, or Firm*—Thomas K. McBride; John F. Spears, Jr.

[57] ABSTRACT

Paraffins or other hydrocarbons are alkylated in a process featuring a reaction zone containing a pool of liquid maintained at its boiling point and containing a suspended solid catalyst, which allows the heat of reaction to vaporize a portion of the liquid phase feed hydrocarbon. The vapor phase withdrawn from the top of the reaction zone is at least partially recycled to the reaction zone either as vapor or liquid. The feed hydrocarbons are introduced to the bottom of the reaction zone as a vapor phase stream, which may contain hydrogen. The catalyst is suspended within the liquid in the reaction zone.

13 Claims, 1 Drawing Sheet

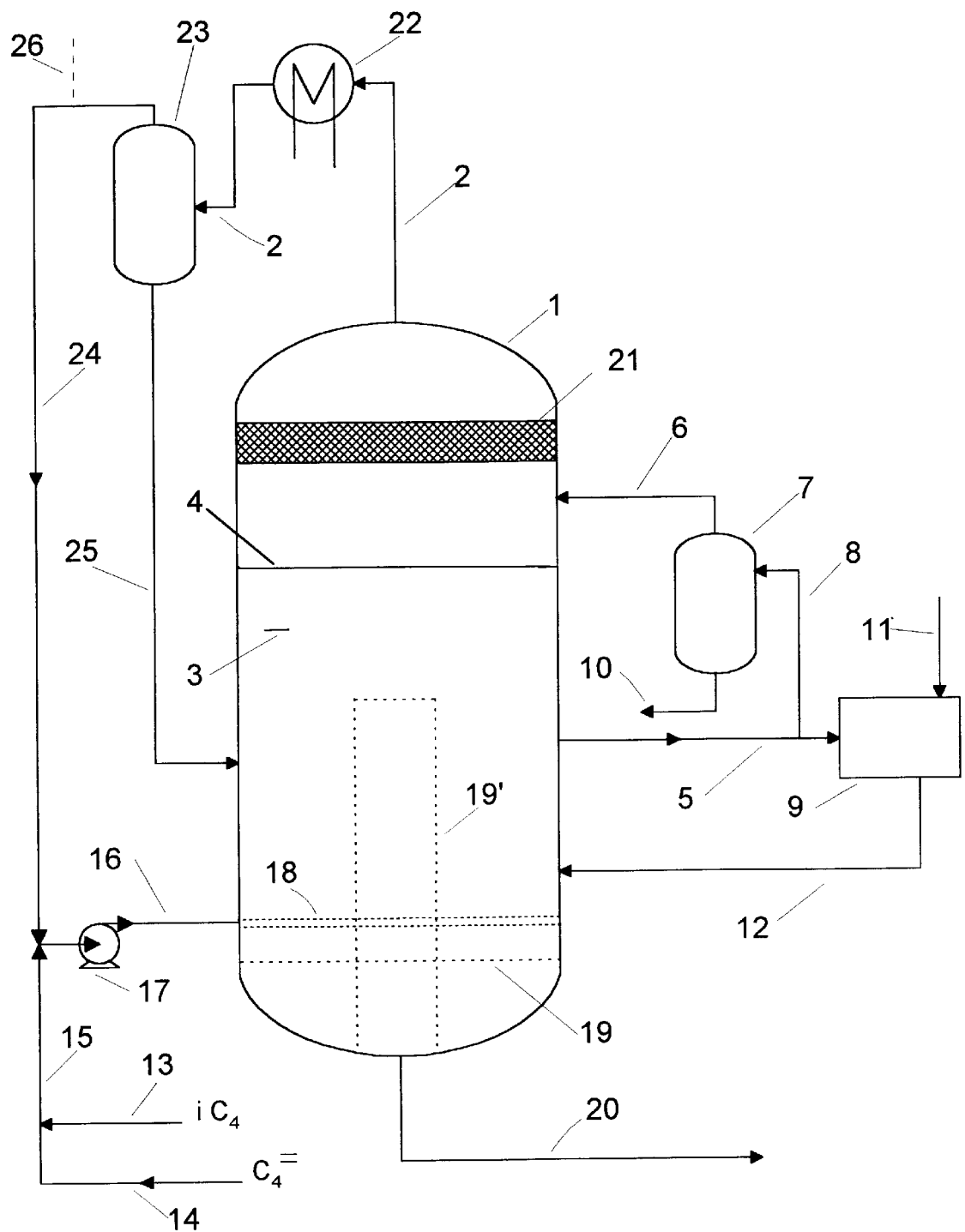

5,856,606

TURBULENT BED SOLID CATALYST HYDROCARBON ALKYLATION PROCESS

BACKGROUND OF THE INVENTION

1. Field of the Invention

The invention relates to a hydrocarbon conversion process. The invention specifically relates to the alkylation of hydrocarbons such as aromatics or paraffins to produce useful chemicals and motor fuel. The invention is primarily directed to a process for the solid bed alkylation of isobutane to produce $C_8$ isoparaffins useful as motor fuel blending components.

2. Related Art

The utility of alkylation reactions and the passage of time has led to the development of a number of effective alkylation technologies which are employed in large scale commercial facilities. One of the most widely used processes for the production of motor fuel is HF alkylation as described in U.S. Pat. No. 4,139,573 issued to D. B. Carson. This reference provides an overview of the HF alkylation process and also describes the use of indirect heat exchange to vaporize butanes as a means of removing heat from the reaction zone.

U.S. Pat. No. 4,849,569 issued to L. A. Smith, Jr. describes a solid bed alkylation process employing catalytic distillation to react a $C_2$–$C_{10}$ olefin with an aromatic hydrocarbon. In catalytic distillation the heat of reaction is allowed to vaporize a portion of the liquid phase reactants present in the mixed-phase conditions of the contacting media present in the reaction zone thereby removing heat from the reaction zone. This patent describes the use of aluminosilicate molecular sieves as a catalyst. U.S. Pat. No. 4,950,834 issued to R. P. Arganbright et al. describes the production of cumene by the reaction of propylene and benzene using two different catalysts in a catalytic distillation zone. The two catalysts contain Y zeolite and omega zeolite respectively.

Yet another design for a solid catalyst alkylation process is described in U.S. Pat. No. 5,133,942 issued to E. M. Jones. This patent describes the use of removable catalyst retained upon distillation trays to perform the alkylation, with a drawoff being provided on each tray for the removal of slurried catalyst. The rising vapor is described as keeping the catalyst in suspension.

U.S. Pat. No. 3,655,813 issued to F. W. Kirsch et al. discloses a motor fuel alkylation process in which a solid catalyst comprising a Y zeolite is withdrawn from the reaction zone passed into a regeneration zone. A slip stream containing reactants and catalysts is passed from the reaction zone to a separation zone and the separated catalyst is then regenerated by combustion. The process appears to be primarily a liquid-phase operation.

U.S. Pat. No. 5,252,613 issued to M. Chang et al. is directed to enhanced catalyst mixing in a bubble column reactor used for exothermic reactions. Rising gas introduced at the bottom of the column provides the majority of the energy involved in dispersing a particulate catalyst in the liquid in the column. A secondary fluid such as recycle gas or condensed light hydrocarbons is introduced above the gas distributing means.

U.S. Pat. No. 4,827,069 issued to J. D. Kushnerick, et al describes a vapor-phase fluidized bed catalytic process for the conversion of a light olefinic gas feedstock to $C_5$-plus hydrocarbons and the conversion of reformate to produce $C_7$–$C_{11}$ aromatic hydrocarbons. Light gas from the top of the reaction zone can be recycled to the reaction zone.

BRIEF SUMMARY OF THE INVENTION

The invention is a solid catalyst alkylation process operated at a pressure which allows vaporization of a reactant to control the temperature of the reaction zone. The invention is characterized by a unique process flow in which the hydrocarbon substrate and alkylating agent are fed to the bottom of a reaction zone as vapor phase stream which causes bubbles of gas to rise through a pool of liquid hydrocarbons retained in the lower portion of the reaction zone. Catalyst is suspended in or ebulated by the liquid in the reaction zone and gradually drawn off for regeneration.

One broad embodiment of the invention may be characterized as a process for the alkylation of a feed hydrocarbon which comprises the steps of passing a vapor-phase feed stream comprising a hydrocarbon having at least two carbon atoms per molecule into a lower portion of a liquid-filled lower section of a reaction zone, with a solid alkylation catalyst being suspended in the liquid present in the lower section of the reaction zone and with the reaction zone being operated at alkylation-promoting conditions including a pressure and temperature which result in the liquid being at its boiling point such that the exothermic reaction of a feed hydrocarbon and an alkylating agent causes the vaporization of liquid phase hydrocarbons present in the reaction zone in the lower section of the reaction zone; removing a vapor phase effluent stream comprising said feed hydrocarbon from a vapor-filled upper section of the reaction zone, cooling and at least partially condensing said effluent stream and separating the resultant liquid and vapor into a first liquid process stream and a first vapor process stream and recycling at least a substantial portion of the first vapor process stream and first liquid process stream into the lower section of the reaction zone; and, withdrawing a second liquid process stream comprising a product hydrocarbon from the lower section of the reaction zone. As used herein the term "substantial"portion is intended to indicate at least 60 and preferably 75 mass percent of the indicated compound or class of compounds.

BRIEF DESCRIPTION OF THE DRAWING

The drawing is a flow diagram of an alkylation unit for the production of motor fuel in a boiling bed of liquid and suspended catalyst located in the lower section of reactor 1.

DETAILED DESCRIPTION AND PREFERRED EMBODIMENTS

Hydrocarbon alkylation is widely used in the petroleum refining and petrochemical industries to produce a variety of useful acyclic and cyclic hydrocarbon products used as motor fuel, plastic and detergent precursors ($C_{10}$–$C_{15}$ linear alkyl aromatics) and petrochemical feedstocks including cumene and ethylbenzene. Much of the installed base of alkylation capacity uses liquid phase hydrofluoric acid, generally referred to as HF, as the catalyst. The petroleum industry continues to use HF acid as the alkylation catalyst of choice due to the high octane fuel it produces together with other operational advantages. The use of HF in these applications has a long record of highly dependable and relatively safe operation. However, the potential damage from an unintentional release of any sizeable quantity of HF and the need to safely dispose of some by-products formed in product or effluent treating procedures has led to an increasing demand for alkylation process technology which does not employ HF as the catalyst. While solid alkylation catalysts are known, they tend to suffer from an unacceptably high deactivation rate which makes frequent regenerations necessary.

It is an objective of this invention to provide a commercially viable alkylation process which does not employ liquid phase HF as the catalyst. It is a further objective of the subject process to provide an alkylation process which counteracts the deactivation of solid alkylation catalysts. It is a specific objective of the subject invention to provide a solid bed motor fuel alkylation process for the production of $C_8$ branched chain hydrocarbons. It is yet another objective of the subject invention to provide a paraffin alkylation process allowing facile on line regeneration of the catalyst and temperature control without requiring extensive and costly internal structures as used in some catalytic distillation processes.

The subject invention achieves these objectives by the use of a unique flow scheme that recycles sizeable amounts of vapor phase hydrocarbon substrate through a liquid-phase reaction zone that is operated at the boiling point of the liquid phase hydrocarbons maintained therein. Catalyst is slurried in the liquid and suspended by the churning action of rising gas bubbles. In limited embodiments of the invention, the alkylation catalyst has a hydrogenation capacity and hydrogen is circulated to selectively hydrogenate $C_6$-plus olefins deposited on the catalyst that are believed at least partially responsible for catalyst deactivation.

A highly active metal hydrogenation component on the catalyst could cause undesired hydrogenation of the feed olefin. This tendency may be counteracted by the composition of the catalyst and by limiting the hydrogen concentration in the reaction zone. It is therefore preferred that the hydrogen/olefin mole ratio in the reaction zone is between 0.01 and 0.1 and more preferably less than 0.05. This hydrogen may be supplied by hydrogen dissolved in liquid returning catalyst from the regeneration zone as described below or by hydrogen addition into the or recycle or feed streams.

The preferred feed hydrocarbon to the subject process is isobutane, which ispreferably reacted with normal butene as an alkylating agent to produce a $C_8$ alkylate for use as gasoline boiling range motor fuel. The feed hydrocarbon or hydrocarbon substrate may vary to include other hydrocarbons including $C_5$ or $C_6$ isoparaffins. Another preferred feed hydrocarbon is benzene, which may be alkylated with a wide range of alkylating agents including ethylene, propylene and butylene to produce such chemicals as ethylbenzene and cumene. A large amount of benzene is also alkylated with higher carbon number olefins having from about ten to about fifteen carbon atoms per molecule to produce linear alkylbenzenes which are then sulfonated to produce detergents. The alkylating agent may be chosen from a variety of compounds including olefins and alcohols. Examples of monohydric alcohols which may be employed as the alkylating agent include ethanol and methanol. Methanol, for instance, is widely described in the literature as being useful in the para selective methylation of benzene and toluene. Suitable feed olefins may have from three to five carbon atoms per molecule.

The overall process flow of the subject invention can be best described by reference to the Drawing. The Drawing is a very simplified flow diagram of a motor fuel alkylation process in which a vapor-phase feed stream comprising normal butenes from line 14 is admixed with a vapor-phase feed stream comprising isobutane from line 13 and then passed into line 15. This vapor-phase mixture of makeup reactants is admixed with the recycled isobutane rich vapor-phase stream from line 24 and then passed via line 16 through a compressor 17 and into a lower section of a vertical alkylation reaction zone 1. The vapor phase stream of line 16 is distributed across the internal volume of the reaction zone by a sparger or distributor 18.

The entering gas is caused to flow into the reaction zone in a manner which causes agitation of the particles of solid catalyst present in the bottom of the alkylation zone. This could be by the release of the gas from the distributor 18 at a high velocity and/or by other means to form bubbles which churn the liquid pool 3 retained in the lower section reaction zone. Vaporization of low boiling compounds or the addition of inert gases are other means to promote bubble formation and catalyst fluidization without mechanical agitation. The liquid pool 3 fills the entire lower section of the vessel up to an interface 4 between the liquid and a volume of vapor retained in the upper section of the vessel. This interface marks the boundary between the lower section and upper section of the apparatus. The lower section may comprise from about 50 to about 85 percent of the internal volume of the vessel 1. The liquid in the reaction zone comprises an admixture of isobutane and product alkylate and dissolved butenes. The catalyst will promote the exothermic alkylation reaction, with the heat released by the reaction leading to vaporization of isobutane and the formation of additional vapor having an equilibrium concentration of all components present in the reactor. The excess vapor phase isobutane from line 16 and the compounds vaporized by the heat of reaction join together to cause a steady flow of gas bubbles upward through the liquid. This promotes admixing of the liquid and a uniform temperature in the liquid. Baffles may be present in the vessel to help promote mixing of the contents of the liquid filled portion of the vessel. The gas bubbles leave the liquid phase and pass upward through the cylindrical reaction zone. The top of the liquid phase is located below the inside upper surface of the vessel to provide a disengagement volume and allow entrained liquid droplets to fall from the rising vapor. An optional mesh blanket 21 may be provided as a demisting pad to remove liquid from the vapor. The isobutane-rich vapor exits the top of the reaction zone via line 2 to be recycled into the bottom of the reaction zone via line 16.

The vapors generated in the reaction zone 1 are removed in line 2. The remaining gas stream is then passed through an indirect heat exchanger 22 wherein heat is removed from the gas and the gas is cooled. As the gas is saturated, some partial condensation will result from the cooling. The stream of line 2 is then passed into the vapor-liquid separator 23 wherein it is divided into a liquid stream carried by line 25 and the vapor stream of line 24. A small portion, less than 20 volume percent, may be removed through optional line 26 to eliminate light gases from the system. The isobutane-rich liquid stream is returned to the reaction zone. This cooling step provides a means of discharging the heat of reaction from the overall process. The cooling may result in an essentially total condensation of the vapor of line 2.

The majority of the $C_8$ product hydrocarbons formed in the reaction zone are dissolved in the liquid phase 3 maintained in the vessel 1, which will have a relatively uniform composition in all parts of the vessel. A screen 19 at the bottom of the reaction zone allows a product stream of the liquid to be separated from the catalyst and removed via line 20 for passage into a fractionation column or other product recovery means. A cylindrical porous centerpipe 19' illustrates another potential configuration for this screen. A slipstream comprising the liquid retained in the reaction zone and suspended catalyst is removed from the lower section of the reactor via line 5 and passed into a catalyst regeneration zone 9 wherein they are contacted with hydrogen to effect olefin saturation. A small stream of liquid and catalyst may be diverted into line 8 and a solids-liquid separation zone 7 such as a cyclone separator or screening device. The separated liquids are returned to the process via line 6. The separated catalyst is removed via line 10. Fresh catalyst may be added via line 11 as needed to maintain a desired catalyst inventory or level of catalyst activity. The regeneration within zone 9 will hopefully be effective enough to result in only a minimal need to withdraw and replace catalyst. The thus regenerated catalyst is then returned to the reaction zone 1 via line 12 together with some process liquid. This liquid may be saturated with hydrogen or have excess hydrogen to maintain any desired hydrogen concentration in the reaction zone.

The exact manner of the regeneration does not form a step in the subject process but is expected to include a "washing" of the catalyst with a liquid phase hydrocarbon such as benzene, possibly at an elevated temperature and preferably in the presence of some hydrogen to remove carbonaceous deposits. The catalyst may, if necessary be contacted with a combustion supporting gas such as air, nitrogen diluted air or ozone to oxidize the carbonaceous deposits which cannot be removed by contact with a liquid phase hydrocarbon. Combustive style regenerations are not preferred. It is preferred that regeneration is performed by contacting the catalyst with hydrogen. The hydrogen is intended to saturate olefinic hydrocarbons on the catalyst and thereby facilitate removal of $C_6$-plus deposits. The regeneration may be mixed-phase or liquid-phase conditions. Regeneration procedures are described in more detail in U.S. patent application Ser. No. 08/43954, which is incorporated herein by reference.

The condensation of gas removed from the reaction zone and the return of the resultant condensate to the reaction zone is the preferred method of removing heat from the reaction zone. This may be augmented by the use of indirect heat exchanger(s) located within the reaction zone or by heat exchangers located outside the reaction zone, with a controlled flow of the reaction zone liquid being pumped through the external heat exchangers. Externally cooled liquid may be added directly to the liquid in the reaction zone or spread across the demisting pad 21.

The passage of the olefin into the reaction zone in a vapor phase stream is intended to inhibit its rapid migration to the active sites of the catalyst thus leading to higher catalyst stability and selectivity. This is due in part from the time delay imparted by the requirement for the olefin to first become absorbed into the liquid phase present in the reaction zone and to then diffuse or move to the surface of the catalyst. The speed of both of these transport phenomena will be increased by the turbulence present in the reactor.

A preferred embodiment of the subject invention can accordingly be characterized as a process for the alkylation of a feed isoparaffin which comprises the steps of passing a vapor-phase feed stream comprising a $C_3$–$C_5$ isoparaffinic feed hydrocarbon and a $C_3$–$C_5$ olefinic hydrocarbon into a liquid filled lower section of a reaction zone, with the reaction zone containing a pool of a liquid comprising the isoparaffinic feed hydrocarbon and a fluidized particulate solid alkylation catalyst and operated at alkylation-promoting conditions which include the presence of hydrogen and a temperature equal to the boiling point of the pool of liquid and reacting the feed hydrocarbon and the olefinic hydrocarbon to produce a branched paraffin product hydrocarbon in an exothermic reaction which causes the vaporization of liquid-phase hydrocarbons present in the pool of liquid; removing a vapor-phase first effluent stream comprising said feed hydrocarbon and said product hydrocarbon from the reaction zone, partially condensing the first effluent stream, and separating the first effluent stream into a liquid phase first process stream, and a vapor phase second process stream which is rich in the feed isoparaffinic hydrocarbon; recycling at least a portion of the first and second process streams into the reaction zone; withdrawing a liquid-phase third process stream, which comprises the product hydrocarbon, from the reaction zone and recovering the product hydrocarbon from the third stream; and, withdrawing a liquid-phase fourth process stream, which comprises the catalyst and the product hydrocarbon, from the reaction zone and regenerating at least a portion of the catalyst present in the fourth process stream by contact with hydrogen in a regeneration zone and then returning the fourth process stream to the reaction zone.

The subject process can be performed using any solid catalyst which is relatively stable at the conditions needed for mixed-phase fluids in the reactor and has the required activity and selectivity for the desired reaction. The catalyst is used in the form of small particles of less than about 0.32 cm (0.125 in) diameter to allow their fluidization. The density of the particles should also be considered, with the particles preferably being only slightly denser than the agitated liquid.

A large number of catalysts have been proposed for the production of motor fuel including various zeolites and superacid catalysts. For instance, U.S. Pat. No. 4,384,161 describes the use of a large pore zeolite and a Lewis acid. The zeolites referred to include ZSM-4, ZSM-3, faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577 . The use of these Lewis acids is not preferred in the subject process as they provide their own waste handling and safety problems. They also will probably require provisions for the circulation of the Lewis acid, which may complicate the process as shown by the just cited U.S. Pat. No. 4,935,577 . U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

It is postulated that a significant portion of the deactivation seen in solid bed alkylation catalysts results from the reaction of the feed olefin(s) to form dimers, trimers or even heavier polymeric entities which clog catalyst pores and/or block catalyst reactive sites. In order to counteract this mode of deaction, it is preferred to use an alkylation catalyst which has a weak hydrogenation function which is selective for the hydrogenation of the olefinic dimers produced on the catalyst. The use of such a catalyst is however not necessary to the performance of the subject process.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The refractory oxide is preferably alumina having a surface area greater than 50 m$^2$/g, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with metal halides. This metal may be chosen from the group consisting of nickel, platinum, palladium, and ruthenium with the first three of these metals being preferred. The catalyst will also contain one or more monovalent metal or alkaline earth metal cations selected from the group consisting of lithium, sodium, potassium, cesium, silver, copper, beryllium, magnesium, calcium and barium. Subsequent to the deposition of these metals and the controlled calcination of the composite, the composite is reacted with a Friedel-Crafts metal halide. The metal may be aluminum, zirconium, tin, tantalum, gallium, antimony or boron. Suitable halides are the fluorides, chlorides and bromides.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 assigned to F. E. Herkes. The use of ZSM-5 zeolites in aromatic alkylation is described in U.S. Pat. No. 3,751,506. ZSM-5 zeolites that have been treated with one or more compounds or elements to improve their selectivity for para-selective alkylation of aromatic hydrocarbons are described in U.S. Pat. No. 4,420,418 . The use of zeolite L, zeolite Omega and zeolite beta as alkylation catalysts for the selective alkylation of benzene is described in U.S. Pat. No. 4,301,316 . The use of a number of natural and synthetic zeolites including clinoptilolite and zeolite Y is described in U.S. Pat. No. 3,251,897 .

Operating conditions suitable for the reaction zone of the subject process include a temperature of about −20 to 60 degrees C, preferably 0 to 20 degrees C, and a pressure as required to maintain at least a major portion (greater than 50 mole %) of the feed hydrocarbon present as a liquid in the presence of the liquid admixture retained in the reaction zone.

It is generally preferred that the process is operated with an excess of the feed hydrocarbon compared to the alkylating agent. That is, it is generally preferred to operate an aromatic hydrocarbon alkylation zone with a ratio of the aromatic hydrocarbon to a feed olefin greater than 1:1, and preferably from about 2:1 to about 5:1 as measured by the flow rates into the reaction zone. Likewise it is preferred to operate with an abundance of isoparaffin compared to alkylating agent in a motor fuel alkylation process. Specifically, it is preferred that the molar ratio of isoparaffin to olefin being charged to the reaction zone is greater than 2:1 and more preferably greater than 3:1. It is recognized that the conditions maintained in the subject mixed-phase reaction zone may influence the actual paraffin:olefin ratio in the liquid phase at the catalyst surface.

What is claimed:

1. A process for the alkylation of a feed hydrocarbon which comprises the steps:
    (a) passing a vapor-phase feed stream comprising a feed hydrocarbon having at least two carbon atoms per molecule into a lower portion of a liquid-filled lower section of a reaction zone, with a solid alkylation catalyst being suspended in the liquid present in the lower section of the reaction zone and with the reaction zone being operated at alkylation-promoting conditions including a pressure and temperature which result in the liquid being at its boiling point such that the exothermic reaction of the feed hydrocarbon and an alkylating agent causes the vaporization of liquid phase hydrocarbons present in the lower section of the reaction zone;
    (b) removing a vapor phase effluent stream comprising said feed hydrocarbon from a vapor-filled upper section of the reaction zone, cooling and at least partially condensing said effluent stream and separating the resultant liquid and vapor into a first liquid-phase process stream and a first vapor-phase process stream and recycling at least a substantial portion of the first vapor-phase process stream and the first liquid-phase process stream into the lower section of the reaction zone; and,
    (c) withdrawing a second liquid process stream comprising a product hydrocarbon from the lower section of the reaction zone.

2. The process of claim 1 further characterized in that the alkylating agent is an olefin and in that a hydrogen concentration providing a hydrogen/olefin mole ratio between 0.01 and 0.1 is maintained in the liquid in the lower section of the reaction zone.

3. The process of claim 1 further characterized in that the feed hydrocarbon is a paraffin.

4. The process of claim 1 further characterized in that the feed hydrocarbon is an aromatic hydrocarbon.

5. The process of claim 1 further characterized in that used catalyst is removed from the reaction zone and replaced by catalyst having a higher activity during the operation of the process.

6. The process of claim 1 further characterized in that the portion of the vapor phase stream which is recycled into the lower section reaction zone is first admixed with the feed stream comprising the feed hydrocarbon and with the alkylating agent.

7. A process for the alkylation of a feed hydrocarbon which comprises the steps:
    (a) passing a vapor-phase feed stream comprising a paraffinic feed hydrocarbon into a lower portion of a liquid filled lower section of a reaction zone, with a solid alkylation catalyst being suspended in the liquid in the lower section of the reaction zone, with the reaction zone being operated at alkylation-promoting conditions including a temperature equal to the boiling point of the liquid and allowing the exothermic reaction of the feed hydrocarbon and an alkylating agent to cause the vaporization of liquid-phase hydrocarbons present in the liquid in the lower section of the reaction zone;
    (b) at least partially condensing a vapor phase effluent stream comprising said feed hydrocarbon and removed from a vapor-filled upper section of the reaction zone, and recycling substantially all of the resultant condensate stream into the reaction zone as a coolant;
    (c) withdrawing a first process stream comprising a product hydrocarbon from the lower section of the reaction zone and recovering the product hydrocarbon; and,
    (d) withdrawing a second process stream comprising the catalyst and the product hydrocarbon from the lower section of the reaction zone, regenerating at least a portion of the catalyst in the second process stream and then returning the second process stream to the reaction zone.

8. The process of claim 7 further characterized in that the alkylating agent is an olefin.

9. The process of claim 7 further characterized in that substantially all of the vapor-phase effluent stream removed from the reaction zone is condensed and returned to the alkylation zone as coolant.

10. The process of claim 7 further characterized in that the catalyst in the second process stream is regenerated by contact with hydrogen and the second process stream comprises hydrogen when it is returned to the reaction zone.

11. A process for the alkylation of a feed isoparaffin which comprises the steps:

(a) passing a vapor-phase feed stream comprising a $C_3$–$C_5$ isoparaffinic feed hydrocarbon and a $C_3$–$C_5$ olefinic hydrocarbon into a liquid filled lower section of a reaction zone, with the reaction zone containing a pool of a liquid comprising the isoparaffinic feed hydrocarbon and a fluidized particulate solid alkylation catalyst and operated at alkylation-promoting conditions which include the presence of hydrogen and a temperature equal to the boiling point of the pool of liquid and reacting the feed hydrocarbon and the olefinic hydrocarbon to produce a branched paraffin product hydrocarbon in an exothermic reaction which causes the vaporization of liquid-phase hydrocarbons present in the pool of liquid;

(b) removing a vapor-phase first effluent stream comprising said feed hydrocarbon and said product hydrocarbon from the reaction zone, partially condensing the first effluent stream, and separating the first effluent stream into a liquid-phase first process stream, and a vapor-phase second process stream which is rich in the feed isoparaffinic hydrocarbon;

(c) recycling at least a portion of the first and second process streams into the reaction zone;

(d) withdrawing a liquid-phase third process stream, which comprises the product hydrocarbon, from the reaction zone and recovering the product hydrocarbon from the third process stream; and, (e) withdrawing a liquid-phase fourth process stream, which comprises the catalyst and the product hydrocarbon, from the reaction zone and regenerating at least a portion of the catalyst present in the fourth process stream by contact with hydrogen in a regeneration zone and then returning the fourth process stream to the reaction zone.

12. The process of claim 11 further characterized in that the alkylation catalyst comprises a metal component having hydrogenation activity.

13. The process of claim 11 further characterized in that hydrogen is circulated through the reaction zone.

* * * * *